United States Patent [19]

Klearman et al.

[11] Patent Number: 5,311,365
[45] Date of Patent: May 10, 1994

[54] COMBINATION TOOL

[76] Inventors: Hayley M. Klearman, 12529H Lighthouse Way Dr., Creve Coeur, Mo. 63141; Richard Agnew, 1630 Stewart St., Santa Monica, Calif. 90404

[21] Appl. No.: 953,997
[22] Filed: Sep. 29, 1992
[51] Int. Cl.$^5$ .............................. G02B 27/02
[52] U.S. Cl. ...................... 359/804; 359/805
[58] Field of Search ............... 359/802, 803, 804, 805, 359/808, 809, 810, 811, 812

[56] References Cited

U.S. PATENT DOCUMENTS

| | | | |
|---|---|---|---|
| 1,059,868 | 4/1913 | Harrison | 359/805 |
| 1,120,421 | 12/1914 | Strickland | 359/805 |
| 1,216,209 | 2/1917 | Callahan . | |
| 1,269,321 | 6/1918 | Schwarz . | |
| 1,278,995 | 9/1918 | Petro . | |
| 1,765,366 | 6/1930 | Crater . | |
| 1,842,403 | 1/1932 | Hunsaker et al. . | |
| 2,070,798 | 2/1937 | Mason . | |
| 2,117,134 | 5/1938 | Bissell . | |
| 2,387,054 | 10/1945 | Brustolon . | |
| 2,435,741 | 2/1948 | Fleenor . | |
| 2,533,747 | 12/1950 | Thienemann | 359/804 |
| 3,510,204 | 5/1970 | Jack . | |
| 4,071,174 | 1/1978 | Weiner | 359/804 |
| 4,072,407 | 2/1978 | Zeisky . | |
| 4,147,411 | 4/1979 | Barry | 359/805 |
| 4,836,596 | 6/1989 | Owen . | |

FOREIGN PATENT DOCUMENTS

| | | | |
|---|---|---|---|
| 211187 | 7/1984 | Fed. Rep. of Germany | 359/804 |
| 2646243 | 10/1990 | France | 359/804 |

Primary Examiner—John T. Kwon
Attorney, Agent, or Firm—Edwin H. Crabtree; Donald W. Margolis

[57] ABSTRACT

A combination tool providing an ability to inspect a gem or an item of jewelry under magnification for viewing, appraising and identification of flaws. The combination tool is lightweight, portable, and can easily be held and used with one hand. The tool includes a pair of opposing and pivoting assemblies. One of the opposing assemblies is used to support a magnification device such as a jeweler's loupe or a gemologist's loupe. The loupe may be releasably attached to the assembly or fixed in place on the assembly. The other opposing assembly is used to releasably hold a gem or item of jewelry under magnification. The combination tool provides the ability to vary the view through the magnification device and the item under inspection by either telescoping and swiveling the assembly holding the loupe or telescoping and swiveling the assembly holding the gem or item of jewelry.

23 Claims, 2 Drawing Sheets

COMBINATION TOOL

BACKGROUND OF THE INVENTION

The present invention relates in general to tools combining the features of a magnification device and a grasping or holding device and pertains, more particularly, to a combination tool for use by a gemologist or jeweler for inspecting gems or jewelry. The combination tool of this invention is an improvement over the known, conventional tools.

With conventional tools that combine the features of magnifying and grasping it is generally necessary to use only one of the features at a time or the use of either of the features in combination is limited. For example, it is common to use a loupe for inspecting a gem or jewelry while holding the object being inspected between the fingers or the ends of a pair of tweezers.

These conventional tools are constructed using a variety of members for supporting the magnifying member. The magnifying member and the grasping member of conventional tools often do not lend themselves to the unique requirements of a gemologist.

It is desired that the inspection of jewelry, and imperative in the case of the gemologist inspecting a gem for the purpose of appraising the stone, to use a standard 10× magnification for the inspection or appraisal. In fact, many jewelers and gemologist carry their own 10× loupes to insure reliable inspection and appraisal of a gem or item of jewelry.

Another drawback associate with the conventional tools is that if a magnifying member is included in combination with a grasping member, such as tweezers, the magnifying member is located at an end of the tweezers opposite the jaws of the tweezers. When trying to view a gem it is not uncommon to lose or flick an expensive gem off of a counter. This is embarrassing, not to mention potentially costly.

While working with someone untrained in the skill of using a loupe, it often becomes necessary to quickly train that person in the use of a loupe, since it is common for an individual to desire to see for himself or herself if seeking to purchase, sell, or have a gem appraised.

If the gem is to be discussed for its value or its flaws, then it is often necessary to view the gem through the magnification of the loupe, as one skilled would do automatically. Existing tools and procedures are often cumbersome and difficult to by either skilled or the unskilled user.

It often becomes a clumsy task to hold a gem, a diamond for example, with tweezers in one hand and a loupe with the other hand. This awkwardness is compounded by the need for note taking, and filling out the standard forms, particularly while performing an appraisal. Normal methods and means for practicing this skill do not allow for showing a gem with a portable, pocket sized tool to an unskilled person or to place and hold the gem in one position if there is a flaw to be observed.

Existing tools also have a drawback related to the limitations inherent in the manner in which the various tools are combined. The existing tools address problems not related to those particularly related to the needs of a jeweler and provide ways in which to provide a sterile package or to inspect flat objects such as stamps or to adapt magnification to tweezers typically used to remove foreign objects from the skin or beneath the skin.

SUMMARY OF THE INVENTION

Accordingly, it is an object of the present invention to provide a combination tool that is adapted to increase the ability of one relatively unskilled in the use of a loupe to view a gem or piece of jewelry.

Another object of the present invention is to provide a combination tool that is constructed to be light, portable, and durable.

A further object of the present invention is to provide a combination tool that is adapted to display a gemstone or jewelry in a fixed and a secure position with one hand thereby substantially freeing up the other hand for other purposes typically required or desired in the examination or appraisal of a gem.

Still another object of the present invention is to provide a combination tool that may be readily adapted to the use of a jeweler's or a gemologist's personal loupe.

Still a further object of the present invention is to provide a combination tool that is adapted for use with a removable loupe or a loupe that is fixed in place. The combination tool of this invention is characterized by the telescoping and swiveling of loupes affixed to one of two pivoting members.

To accomplish the foregoing and other objects of this invention there is provided a combination tool for grasping and inspecting an object, such as a gem or piece of jewelry, that comprises a pair of members connected with a pivoting means. One member of the pair includes means for grasping the object. The other of the pair of members includes means for inspecting the object under magnification. The magnification means is removable from the pivoting members in one preferred embodiment.

The tool may have any one of a number of magnifying means arrangements in addition to the embodiment in which the magnifying means is provided by adapting a conventional loupe which is removable from the tool for separate use of the loupe. In this way the jeweler or gemologist has a choice to use his or her own loupe or to have tool with a loupe affixed to a rod member. In a preferred embodiment the loupe telescopes and/or pivots on the rod to which it is attached.

There is also additionally provided a conventional grasping means for the gem or jewelry. In the disclosure and drawings of the present invention there is provided five preferred embodiments. Each of the preferred embodiments incorporates the features of the invention except a removable loupe.

These and other objects and features of the present invention will be better understood and appreciated from the following detailed description of embodiments thereof, selected for purposes of illustration and shown in the accompanying drawings.

DETAILED DESCRIPTION

Figure 1:
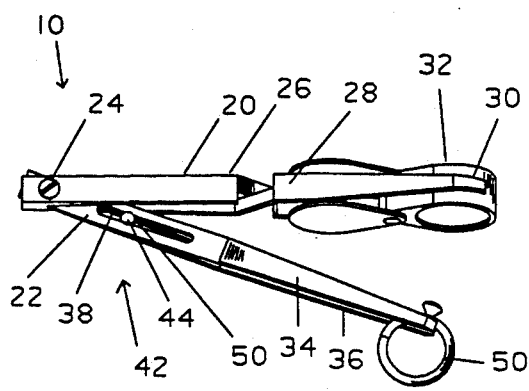
FIG. 1 is a side view of one embodiment of a combination tool constructed in accordance with the present invention depicting a removable loupe.
Figure 2:
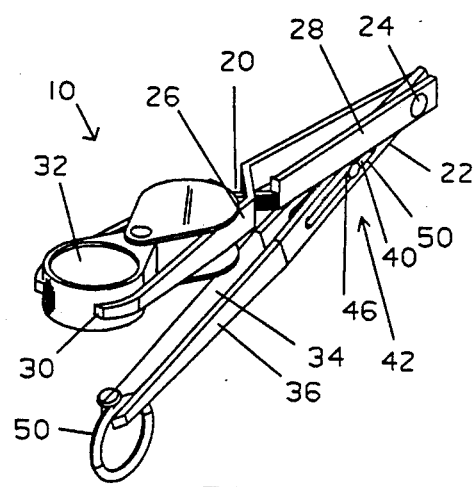
FIG. 2 is a perspective view of the combination tool depicted in FIG. 1.
Figure 3:
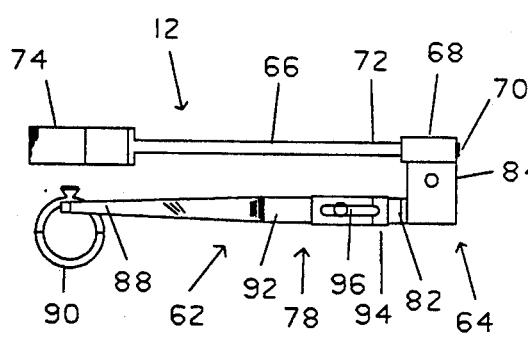
FIG. 3 is a side view of another embodiment of a combination tool constructed in accordance with the present invention depicting a telescoping and rotating loupe.
Figure 4:
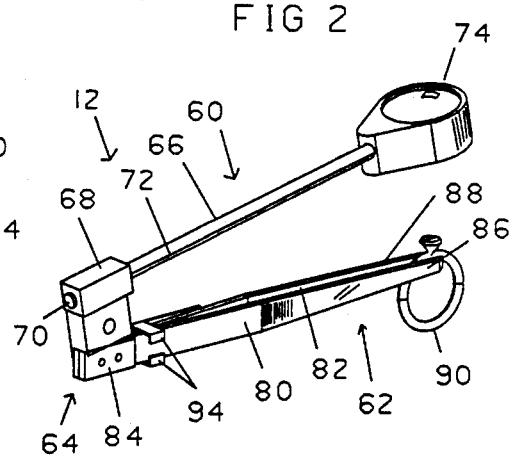
FIG. 4 is a perspective view of the combination tool depicted in FIG. 3.
Figure 5:
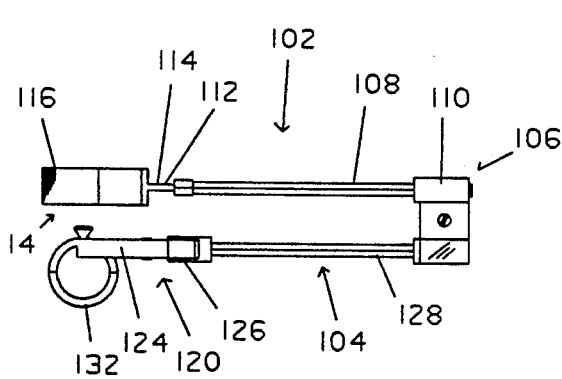
FIG. 5 is a side view of another embodiment of a combination tool constructed in accordance with the present invention depicting a telescoping and rotating loupe and a basket for grasping a gem or piece of jewelry.
Figure 6:
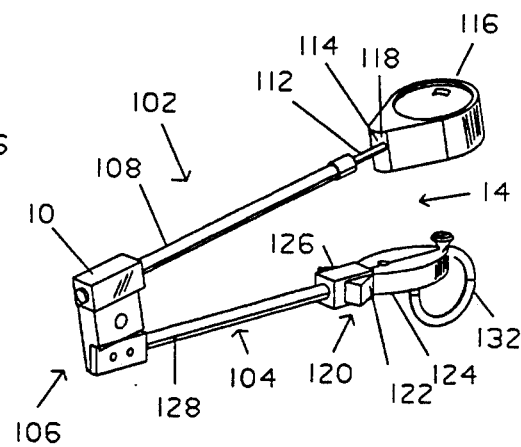
FIG. 6 is a perspective view of the combination tool depicted in FIG. 5.
Figure 7:
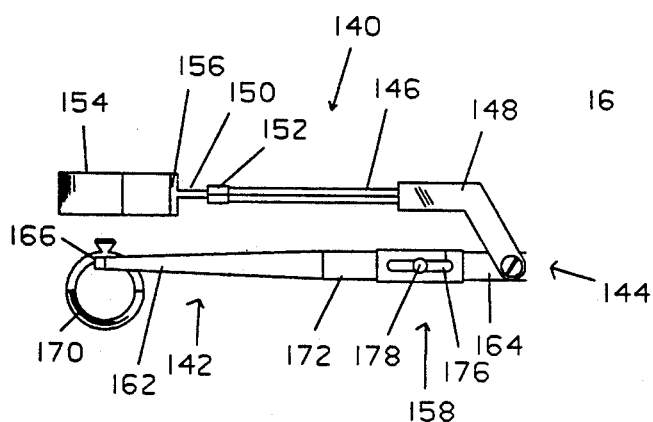
FIG. 7 is a side view of another embodiment of a combination tool constructed in accordance with the present invention depicting a telescoping and rotating loupe and a pair of tweezers with a locking mechanism for grasping a gem or piece of jewelry.
Figure 8:
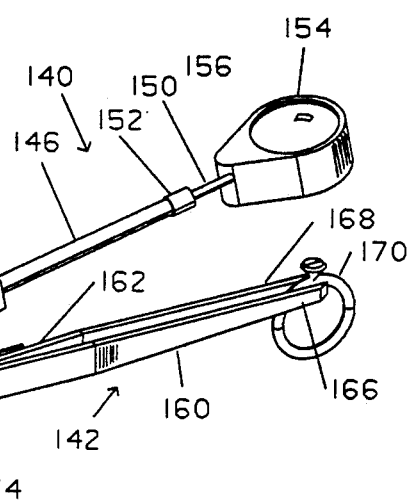
FIG. 8 is a perspective view of the combination tool depicted in FIG. 7.
Figure 9:
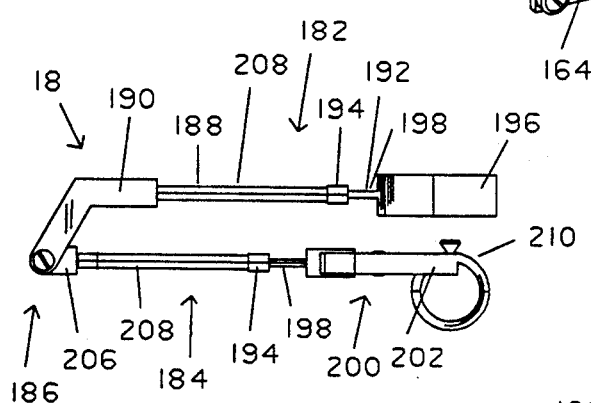
FIG. 9 is a side view of another embodiment of a combination tool constructed in accordance with the present invention depicting a telescoping and rotating loupe and a basket for grasping a gem or piece of jewelry.
Figure 10:
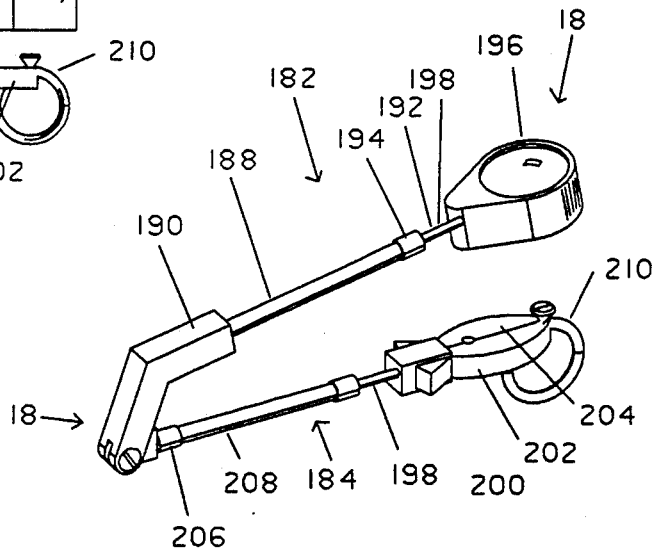
FIG. 10 is a perspective view of the combination tool depicted in FIG. 9.

Referring now to the drawings there are shown preferred embodiments for the combination tool of this invention. The combination tool is described in connection with a gemology application to inspect a gem or jewelry. The combination tool of the present invention is particularly adapted for providing enhancements to the inspection of gems for value and to find and describe flaws and is characterized by the ability to view and manipulate the gem or piece of jewelry with one hand, whether or not skilled in the use of a jeweler's loupe.

The drawings show preferred embodiments of the combination tool 10, 12, 14, 16, and 18. Referring first to embodiment 10, the combination tool is shown in conjunction with one pivoting member 20 and another pivoting member 22 connected by a an intermediate pivot means including intermediate pivot 24, having a screw and nut combination as illustrated in these and subsequent drawings figures.

The one member includes a first arm 26 and a second arm 28 at the end of which are located a pair of normally closed jaws 30. A jeweler's loupe 32 with an enclosure or housing piece is removable and held in by the closed jaws. The other member includes a first tweezer member 34 and an opposing tweezer member 36. The tweezer members are locked with a conventional closure mechanism consisting of a slot 38 on the one tweezer member and an opposing slot 40 on the opposing tweezer member.

A tightening rivet 42 is carried in the slots 38 and 40. The tightening rivet has a first head 44 and an opposing head 46 and an intermediate shaft member. The shaft member is not shown in the drawings. Sliding the rivet in the slot pulls the opposing tweezer members together and effectively locks the opposing tweezer members onto a ring 50 or other jewelry item, gem, or other precious or semi-precious stone.

The embodiment 12 includes a loupe assembly 60 and a gem holding assembly 62 and an intermediate pivot assembly 64. The loupe assembly includes a rod member 66 and a pivot attachment assembly 68. Pivot assembly components 70 connect the rod member 66 at end 72. Rod member 66 connects to a loupe or other magnifying means 74.

The gem holding assembly 62 includes a slide mechanism 78 for locking or securing together opposing gem holding assembly arms 80 and 82. The arms of the gem holding assembly are connected to a pivot attachment member 84.

The gem holding assembly 62 has a pair of opposing gem holding jaws 86, 88 for securely grasping a gem or item of jewelry 90. The slide mechanism that holds the jaws together on the gem, etc. includes a finger slide member 92 associated with a slot and pin arrangement 96 and a plurality of bent extension members 94. This form of a mechanism is conventional and found in existing tweezer arrangements.

The preferred embodiment of the present invention depicted in the drawings and identified with reference character 14 includes a loupe assembly 102, a gem holding assembly 104, and an intermediate pivot assembly 106.

The loupe assembly includes a base member or sleeve 108, a pivot attachment member 110, and a telescoping member 112. An end 114 of the telescoping member is attached to a loupe 116 or other magnifying means. The telescoping member and loupe are joined by an assembly 118 that is appropriate for the members of the loupe assembly. A preferred embodiment is illustrated and described in subsequent drawings.

The gem holding assembly includes a basket or stone holding assembly 120 for holding which is a proprietary item and is sold by Gem Instruments Corporation. The basket assembly or its equivalent will include one gem holding arm 122 and another gem holding arm 124 connected by an intermediate pivot attachment 126 and the arms are normally biased together by a spring (not shown). The basket is grasping a gem or other item of jewelry 132. The pivot attachment 126 is connected to a rod member 128. The rod member 128 is secured to the pivot attachment member 110.

The preferred embodiment 16 of the present invention illustrated in the attached drawings includes a loupe assembly 140, a gem holding assembly 142, and an intermediate pivot assembly 144. The loupe holding assembly includes a base member or sleeve 146 with a pivot attachment member 148 and a telescoping member 150.

An adjustment cap and sleeve assembly 152 allows for the extension of the telescoping member and secures the telescoping member in the desired position. A loupe 154 or other equivalent magnifying means is located at the free end of the telescoping member and connected by an attachment assembly 156.

There are a number of locking mechanisms to use on the gem holding assembly. In preferred embodiment 16 sliding mechanism 158 is illustrated for locking or securing the gem holding assembly. The latter includes one gem holding arm 160 and another gem holding arm 162 with an associated pivot attachment member 164. A pair of jaws 166 and 168 grasp a piece of jewelry or a gem 170. The pair of jaws is held together by an appropriate securing mechanism. The securing mechanism can be one of any number of known securing mechanisms.

In the preferred embodiment illustrated in the attached drawings includes jaws held together by using a finger slide 172 and a plurality of bent extension members 174 that bend around the opposing arms of the gem holding assembly. The slide has a slot and a pin 178 slides in the slot and pulls the jaws together as the slide is moved towards the jaws.

The preferred embodiment 18 of the combination tool of the present invention includes a loupe assembly 182 and a gem holding assembly 184 with an intermediate pivot assembly 186. The loupe assembly includes a base member or rod 188, a pivot attachment member 190, and a loupe attachment end 192. If a telescoping member was used then it would include the adjustment cap and sleeve assembly 194 and a telescoping member 198 (identified by the dashed line).

A loupe 196 or other magnifying means is located either at the end of the base member 188 or at the end of the telescoping member as described for another preferred embodiment.

The gem holding assembly has another telescoping member 198 with a known basket or stone holder assembly 200 as previously described. The basket assembly includes a pair of spring-biased arms 202, 204 attached for holding the object to be inspected. The gem holding assembly further includes a pivot attachment member 206 and a pivoting rod or sleeve 208. A piece of jewelry or a gem or stone 210 is held in the basket for inspection and/or appraisal.

In operation, in connection with the inspection of gems or pieces of jewelry previously mentioned to appraise and/or inspect for flaws, the gem is held by the tweezers or the basket. If the tweezers are used and they include one of the securing assemblies or equivalent, then the gem or jewelry is grasped by the tweezer jaws and held in place with the securing assembly hold the jaws together. If the proprietary basket is used, then the basket closed on the gem or jewelry and holds it for inspection.

The first described preferred embodiment includes a loupe assembly in which the loupe is removable but held or secured in place and the loupe is used for magnified inspection of the gem or jewelry. The reverse angle of the normally closed, spring-biased jaws hold the loupe until released. The other described preferred embodiments illustrate examples of the loupe attached to the end of a rod that may telescope and swivel, thereby increasing the flexibility of the use of the combination tool of this invention.

In particular preferred embodiments of the present invention the object (e.g., gem or jewelry) holding means is also attached to a telescoping rod and may swivel. These arrangements allow inspecting the object at various angles and from different perspectives.

From the foregoing description those skilled in the art will appreciate that all of the objects of the present invention are realized. A combination tool has been shown and described for providing the ability to inspect a gem or an item of jewelry under magnification for viewing or appraising or identification of flaws. The grasping of the gem, etc. and the securing of a loupe to the assembly, whether or not removable, allows one relatively unskilled in the use of a loupe to view a gem or piece of jewelry under magnification.

The combination tool is constructed to be light, portable, and durable and easily held and used with one hand. An embodiment of the present invention that incorporates the removable loupe assembly allows the use of a jeweler's or a gemologist's personal loupe.

The present invention further provides a combination tool adapted for use with either a removable loupe or a loupe that is fixed in place. The combination tool provides the ability to vary the view through the magnifying means by the use of the telescoping and swiveling of loupes affixed to one of two pivoting members and the telescoping and swiveling of the means for holding the inspected object.

While specific embodiments have been shown and described, many variations are possible. The particular assembly used, either loupe or holding means, can be matched with another desired assembly. Thus, it will be seen that more than the five configurations shown and described can be constructed from the variety of assemblies shown and described herein by variously combining the loupe assemblies and the holding assemblies.

The invention incorporates a magnifying means that is preferably a jeweler's loupe. The loupe is preferably a 10x loupe, primarily since official appraisals by certified appraisers requires the 10x loupe for standardization of inspection.

The particular shape of the combination tool or any of its assemblies or sub-assemblies including all dimensions, materials, and finishes may vary although a combination of dimensions, materials and finishes are preferred so far as they are specified in the drawing figures depicting the various assemblies and components.

Having described the invention in detail, those skilled in the art will appreciate that modifications may be made of the invention without departing from its spirit. Therefore, it is not intended that the scope of the invention be limited to the specific embodiments illustrated and described. Rather, it is intended that the scope of this invention be determined by the appended claims and their equivalents.

What is claimed is:

1. A tool combining the features of holding an object while inspecting the object, comprising:
   a first member;
   means for inspecting an object carried by the first member, the first member includes a pair of opposing members the opposing members biased relative to each other, the opposing members normally biased toward each other, whereby the inspecting means is removable from the first member;
   a second member;
   means for holding the object relative to the inspecting means; the holding means associated with the second member; and
   means for moving the holding means relative to the inspecting means by pivoting the first member relative to the second member.

2. A tool as set forth in claim 1 wherein the object is removable from the holding means.

3. A tool as set forth in claim 1 wherein the holding means and the second member are combined, the combined holding means and second member providing a pair of opposing members normally biased apart, one opposing member from the other opposing member, the holding means including a pair of normally spaced apart end portions located generally at the ends of the respective opposing members.

4. A tool as set forth in claim 1 wherein the first member includes a telescoping assembly.

5. A tool as set forth in claim 4 wherein the inspecting means is carried by the telescoping assembly.

6. A tool as set forth in claim 1 wherein the inspecting means is rotatable.

7. A tool as set forth in claim 1 wherein the second member includes a telescoping assembly.

8. A tool as set forth in claim 7 wherein the holding means is carried by the telescoping assembly.

9. A tool as set forth in claim 1 wherein the holding means is rotatable.

10. A tool for holding and inspecting an object, comprising:

a first member;
a second member;
a pivot assembly intermediate the first member and the second member;
magnifying means carried by the first member, the first member is a pair of tweezers, the tweezers including a pair of biased apart members, the tweezers further including respective end portions bent to provide normally closed jaw members, whereby the normally closed jaws members grasp the removable magnifying means; and
holding means carried by the second member.

11. A tool as set forth in claim 10 wherein the holding means and the second member are combined, the combined holding means and second member providing a pair of opposing, normally biased apart tweezer members, the holding means including a pair of normally spaced apart end portions located generally at the ends of the respective opposing tweezer members.

12. A tool as set forth in claim 10 wherein the first member includes a telescoping assembly.

13. A tool as set forth in claim 12 wherein the magnifying means is carried by the telescoping assembly.

14. A tool as set forth in claim 10 wherein the magnifying means is rotatable.

15. A tool as set forth in claim 10 wherein the second member includes a telescoping assembly.

16. A tool as set forth in claim 15 wherein the holding means is carried by the telescoping assembly.

17. A tool as set forth in claim 10 wherein the holding means is rotatable.

18. A method of holding an object while inspecting the object, comprising the steps of:
grasping an object to be inspected with one member;
supporting a means for inspecting the object with another member;
pivoting the one member relative to the other member;
adjusting the view of the inspecting means relative to the object; and
squeezing open a pair of normally closed jaws to release the means for inspecting the object.

19. A method as set forth in claim 18 further comprising the step of squeezing together a pair of normally open jaws to grasp the object for inspection.

20. A method as set forth in claim 18 further comprising the steps of:
telescoping the one member and the inspecting means relative to the other member; and
adjusting the view of the inspecting means relative to the object.

21. A method as set forth in claim 18 further comprising the steps of:
telescoping the other member and the object relative to the one member; and
adjusting the view of the object relative to the inspecting means.

22. A method as set forth in claim 18 further comprising the steps of:
rotating the one member and the inspecting means relative to the other member and the object; and
adjusting the view of the inspecting means relative to the object.

23. A method as set forth in claim 18 further comprising the steps of:
rotating the other member and the object relative to the one member and the inspecting means; and
adjusting the view of the object relative to the inspecting means.

* * * * *